United States Patent
Opin et al.

(10) Patent No.: US 7,442,039 B2
(45) Date of Patent: Oct. 28, 2008

(54) ORTHODONTIC BRACKET AND CLIP RELEASE TOOL

(75) Inventors: Perry Opin, Milford, CT (US); Shingo Katayose, Futaba-gun (JP); Kousei Endo, Futaba-gun (JP); Masaaki Orikasa, Futaba-gun (JP)

(73) Assignee: Tomy Incorporated, Fukushima-ken (JP)

( * ) Notice: Subject to any disclaimer, the term of this patent is extended or adjusted under 35 U.S.C. 154(b) by 78 days.

(21) Appl. No.: 10/730,268

(22) Filed: Dec. 9, 2003

(65) Prior Publication Data

US 2004/0166458 A1 Aug. 26, 2004

Related U.S. Application Data

(60) Provisional application No. 60/431,693, filed on Dec. 9, 2002.

(51) Int. Cl.
*A61C 3/00* (2006.01)
(52) U.S. Cl. .................... 433/11; 433/3; 433/8; 433/10; 433/13
(58) Field of Classification Search .................. 433/11, 433/3, 13, 10, 8
See application file for complete search history.

(56) References Cited

U.S. PATENT DOCUMENTS

| 3,076,265 | A | * | 2/1963 | Moore | 433/11 |
| 4,698,017 | A | | 10/1987 | Hanson | |
| 5,562,444 | A | | 10/1996 | Heiser et al. | |
| 5,586,882 | A | * | 12/1996 | Hanson | 433/13 |
| 5,906,486 | A | | 5/1999 | Hanson | |
| 6,071,118 | A | * | 6/2000 | Damon | 433/9 |
| 6,071,119 | A | * | 6/2000 | Christoff et al. | 433/14 |
| 6,168,428 | B1 | * | 1/2001 | Voudouris | 433/11 |
| 6,193,508 | B1 | * | 2/2001 | Georgakis | 433/11 |
| 6,776,613 | B2 | * | 8/2004 | Orikasa | 433/11 |
| 2001/0005574 | A1 | * | 6/2001 | Manemann et al. | 433/11 |
| 2002/0006595 | A1 | * | 1/2002 | Voudouris | 433/4 |
| 2002/0119414 | A1 | * | 8/2002 | Orikasa | 433/10 |

* cited by examiner

*Primary Examiner*—Ralph Lewis
*Assistant Examiner*—Jonathan Werner
(74) *Attorney, Agent, or Firm*—Sughrue Mion, PLLC

(57) ABSTRACT

An orthodontic bracket has a clip which is curved substantially in U-shape as covering at least one part of an opposite side to a base in an arch wire slot. Catching end portions which are provided at an upper end part of the clip may be caught to enable to creep under a cover portion supported by the bracket main body. The clip is formed at the upper end part thereof with a concave portion as a recess portion which enables to catch a clip release tool for releasing the clip.

15 Claims, 16 Drawing Sheets

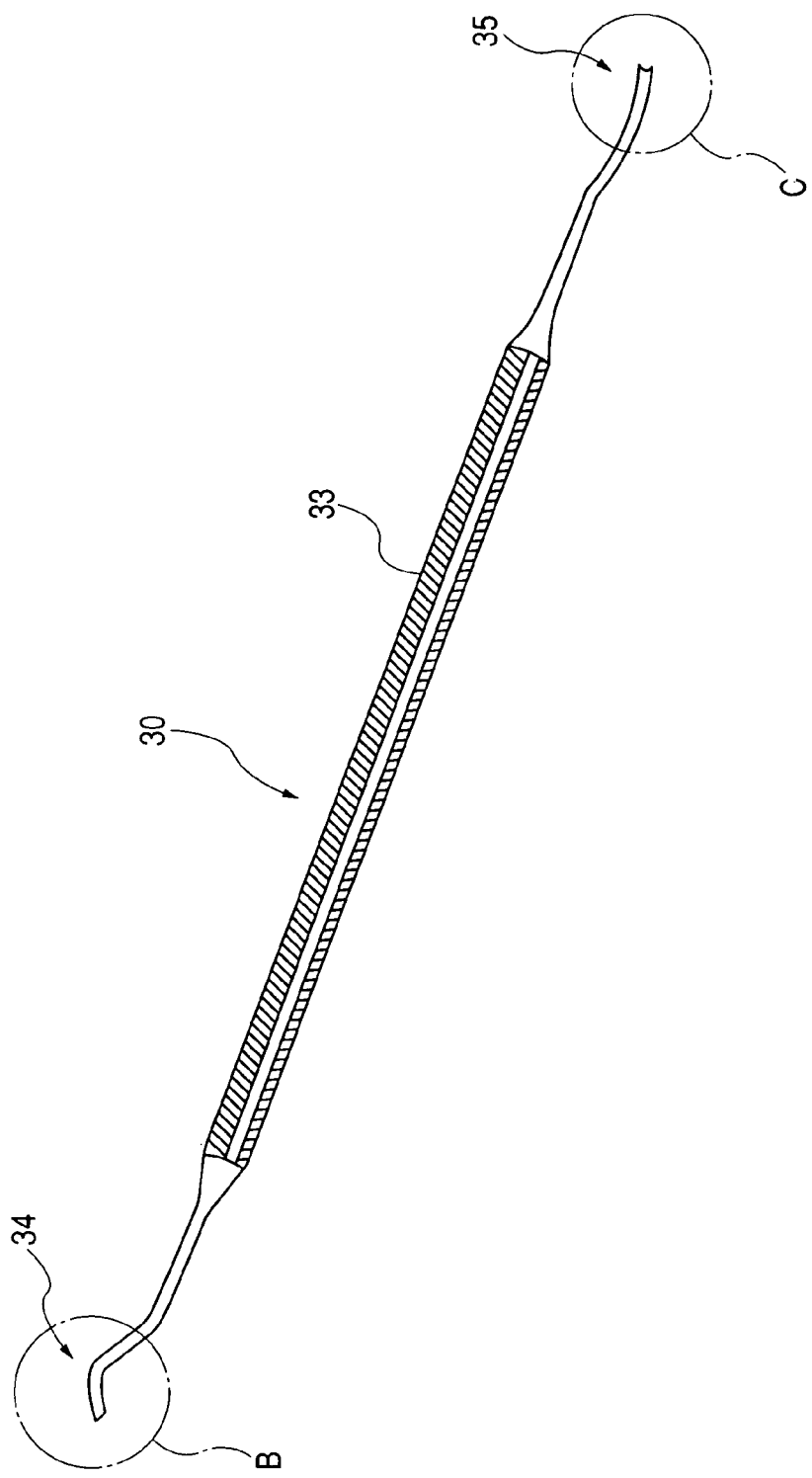

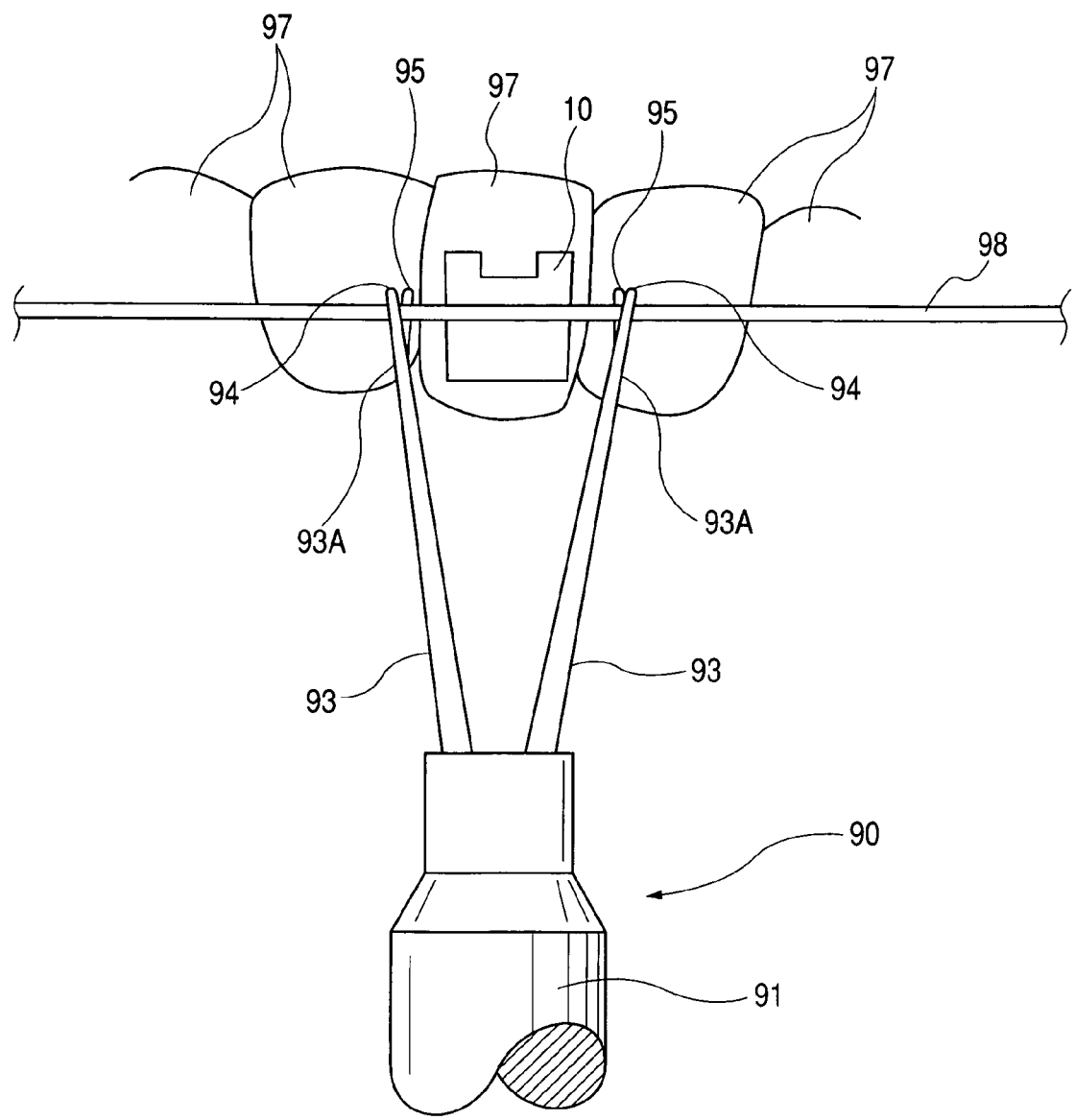

ORTHODONTIC BRACKET AND CLIP RELEASE TOOL

This application claims benefit of Provisional Application No. 60/431,693 filed Dec. 9, 2002; the disclosure of which is incorporated herein by reference.

BACKGROUND OF THE INVENTION

1. Field of the Invention

The present invention relates to an orthodontic bracket and a clip release tool, and in particular, for correcting irregular teeth rows or twisted teeth, relates to an orthodontic bracket and a clip release tool.

2. Description of the Related Art

In general, the orthodontic bracket has been used for correcting teeth rows. As to the orthodontic bracket, a base thereof is provided with a bracket main body. The bracket main body is formed with an arch wire slot for receiving an arch wire therein and is furnished with a clip for preventing the arch wire from getting out from the interior of arch wire slot.

The clip is curved substantially in U-shape and is formed to be engageable in such a manner that a catching end portion formed at an upper distal portion of the clip creeps under a catching part of the bracket main body.

As means for taking off the upper distal portion of the clip from the catching part, the following technologies are disclosed.

For example, U.S. Pat. No. 4,698,017 shows an art of rotating a clip by a bar-like tool to release the arch wire slot.

U.S. Pat. No. 5,562,444 shows an art of releasing a clip rotating round a tie-wing by the bar-like tool inserted in a hole of the clip.

This publication also discloses a way of pushing to open the front end of the clip by use of a tool (not especially designated).

In addition, U.S. Pat. No. 5,906,486 is concerned with a self-ligation bracket of sliding a U-shaped clip and releasing and closing the arch wire slot, and shows an art of inserting the bar-like tool into the hole of the clip for releasing the clip.

The self-ligation bracket is meant by a bracket where an opening of the arch wire slot is closed with a rotating or sliding clip so that the arch wire does not get out from the interior of the arch wire slot.

But, when releasing the clip by the bar-like tool inserted in the hole of the clip, it is necessary to work the bar-like tool as a lever, and so an exceeding load is effected on the clip.

Therefore, when releasing the clip by the bar-like tool, the clip is often deformed.

In case the clip is deformed, even if returning the clip to a closing position, not only the deformed clip cannot press down the arch wire, but also the arch wire gets out of position not to continue a curing.

Further, since the hole into which the bar-like tool is inserted is formed at about center of the clip, a spring property of the clip is spoiled to reduce force pressing down the arch wire, and besides a problem arises that the clip is easily deformed owing to concentration of stress.

SUMMARY OF THE INVENTION

In view of the above mentioned problems, the invention has been realized. Accordingly it is an object of the invention to offer an orthodontic bracket which enables to prevent the clip from deforming when releasing the clip, and a clip release tool.

For accomplishing the above mentioned object, the orthodontic bracket of a first aspect of the invention comprises, a base firmly attachable directly or indirectly to teeth surfaces;

a bracket main body equipped on one side of the base;

an arch wire slot shaped in groove along mesiodistal direction in the bracket main body, enabling to support an arch wire therein;

a substantially belt-like clip curved substantially in U-shape as covering at least one part of an opposite side to the base in the arch wire slot, the clip having a catching end portion for creeping under a cover portion supported by the bracket main body at an upper end part thereof and a recess portion for catching a clip release tool for releasing the clip at the upper end part thereof; and a guide portion formed in at least one of the bracket main body and the base and along a tooth axial direction crossing with the arch wire slot, enabling to guide the clip.

Herein, the orthodontic bracket according to the invention includes an embodiment that the bracket main body is secured to the face-like base attachable to the teeth surfaces, or an embodiment that the bracket main body is welded, via the base, to a band attached to the teeth surfaces.

In the thus structured orthodontic bracket, the clip is provided at the upper end part thereof with the recess portion which enables to catch the clip release tool for releasing the clip. The position catching the clip release tool is formed to be the recess, so that it is not required to open a hole for the clip to pass through in the thickness direction. Thus, although the clip is substantially U-shaped and narrow in width, it keeps rigidity and can secure spring force to press down the arch wire.

Besides, since the clip is not opened with the hole but formed with the recess portion, concentration of stress is reduced with respect to the clip, and the clip can be prevented from deformation.

According to the orthodontic bracket of a second aspect of the invention, in the orthodontic bracket of the first aspect, it is desirable that the recess portion is a concave portion which is formed at the upper end part of the clip and does not pass through the clip along thickness.

The recess portion is made the concave, whereby the clip can be released while being pressing it to the bracket main body, so that the clip is not caused to be deformed, and the recess portion can be comparatively easily formed.

According to the orthodontic bracket of a third aspect of the invention, in the orthodontic bracket of the first aspect, desirably the recess portion is a cut-and-rising portion where the clip rises along thickness in a direction separating from the bracket main body.

The recess portion is made the cut-and-rising portion by rising in a direction separating from the bracket main body, so that the recess portion can be comparatively easily formed. The clip can be released while being pressing it to the bracket main body by use of an exclusively used tool.

According to the orthodontic bracket of a fourth aspect of the invention, in the orthodontic bracket of the third aspect, desirably the recess portion is the cut-and-rising portion where one side of a slit as a boundary formed at the upper end part of the clip rises along thickness in a direction separating from the bracket main body.

The recess portion is the cut-and-rising portion which causes one side of the slit as the boundary in the direction separating from the bracket main body, whereby the recess portion is comparatively easily formed. In addition, thereby, seeing the slit as the boundary, its front side can be a convex and its inner part can be a concave, so that though not being the exclusively used tool, the clip can be released while being pressing it to the bracket main body.

According to the orthodontic bracket of a fifth aspect of the invention, in the orthodontic bracket of the third aspect, desirably the recess portion is formed at an end part of the clip.

The recess portion is formed at the end part of the clip, whereby the clip can be more easily formed, and the exclusively used tool can be positioned accurately at its front end.

According to the orthodontic bracket of a sixth aspect of the invention, in the orthodontic bracket of the fifth aspect, desirably the recess portion is shaped substantially in a half-spherical dome.

The recess portion is shaped substantially in the half-spherical dome, whereby the clip release tool can be properly caught by the recess portion, making use of the substantially half-spherical dome.

According to the orthodontic bracket of a seventh aspect of the invention, in the orthodontic bracket of the sixth aspect, desirably the recess portion has a cutout substantially in V-shape at a flat and end part thereof.

The recess portion is formed with the cutout, whereby the cutout portion holds the release tool so that the recess portion surely catches the release tool. Therefore, the clip can be more easily released when the clip is released.

The orthodontic bracket of an eighth aspect of the invention comprises, a base firmly attachable directly or indirectly to teeth surfaces;

a bracket main body equipped on one side of the base;

an arch wire slot shaped in groove along mesiodistal direction in the bracket main body, enabling to support an arch wire therein;

a substantially belt-like clip curved substantially in U-shape as covering at least one part of an opposite side to the base in the arch wire slot, the clip having a catching end portion for creeping under a cover portion supported by the bracket main body at an upper end part thereof and a catching cutout portion substantially in V-shape for catching a clip release tool for releasing the clip at the upper end part thereof; and a guide portion formed in at least one of the bracket main body and the base and along a tooth axial direction crossing with the arch wire slot, enabling to guide the clip.

The clip is formed at the upper end part thereof with a catching cutout portion substantially in V-shape which enables to catch the clip release tool for releasing the clip, whereby the recess portion can be more easily formed. The clip can be easily formed, while the spring force of the clip can influence over the catching ends formed at the upper end parts of the clip extending to both of mesial and distal sides. Therefore, rotation control of the arch wire can be effectively exercised.

According to the orthodontic bracket of a ninth aspect, in the orthodontic bracket of the first aspect or the eighth aspect, the clip has a contacting portion and the bracket main body has a receiving portion enabling to contact to the contacting portion, and wherein when the clip is released from the bracket main body, the contacting portion contacts to the receiving portion, thereby enabling to regulate a releasing position of the clip from the bracket main body.

The releasing position of the clip from the bracket main body by the contacting portion and the receiving portion is enabled to be regulated, whereby it is possible to prevent the clip from exceedingly releasing or dropping from the bracket main body.

The clip release tool of a tenth aspect of the invention, for releasing a clip from a bracket main body of an orthodontic bracket, the orthodontic bracket comprising a base firmly attachable directly or indirectly to teeth surfaces, a bracket main body equipped on one side of the base, an arch wire slot shaped in groove along mesiodistal direction in the bracket main body, enabling to support an arch wire therein, a substantially belt-like clip curved substantially in U-shape as covering at least one part of an opposite side to the base in the arch wire slot, the clip having a catching end portion for creeping under a cover portion supported by the bracket main body at an upper end part thereof and a recess portion or a substantially V-shaped catching cutout portion for catching a clip release tool for releasing the clip at the upper end part thereof, and a guide portion formed in at least one of the bracket main body and the base, and along a tooth axial direction crossing with the arch wire slot, enabling to guide the clip, the clip release tool comprising:

a first projection and a second projection which are arranged substantially in V-shape, wherein the first projection enables to catch the recess portion or the substantially V-shaped catching cutout portion of the clip, and the second projection regulates the engagement of the first projection with the recess portion or the catching cutout portion, while pressing down the clip to prevent the clip from deformation of the clip.

The clip release tool comprises the first projection and the second projection arranged substantially in V-shape. The first projection is caught with the recess portion or the catching cutout potion, and the second projection regulates the engagement of the first projection with the recess portion or the catching cutout portion.

Pressing the clip with the second projection, when releasing the clip, the clip is prevented from tuning up and deformation.

BRIEF DESCRIPTION OF THE DRAWINGS

FIG. 4 is a perspective view showing a clip release tool according to the invention;

FIG. 18 is a view for explaining the using example of the clip release tool according to the invention.

DETAILED DESCRIPTION OF THE INVENTION

Explanations will be made to embodiments according to the invention, referring to the attached drawings. In each of the following embodiments, members and others having explained in FIG. 1 will be given the same numerals or corresponding marks in other drawings for simplifying or omitting the explanation.

Herein, in each of under shown embodiments, as the orthodontic bracket, a twin bracket (the bracket having the two cover portions) is exemplified, but the invention is also applicable to a single bracket, and is not limited to the twin bracket only.

In addition, in the following embodiments, the orthodontic bracket used to a labial side (a lip side) is shown, but also applicable to a lingual side (a tongue side).

Further, the invention is titled as the orthodontic bracket, but the bracket referred to herein includes a buccal tube for molars, and is not meant by brackets of narrow meaning as for anterior teeth or bicuspids.

Figure 1:
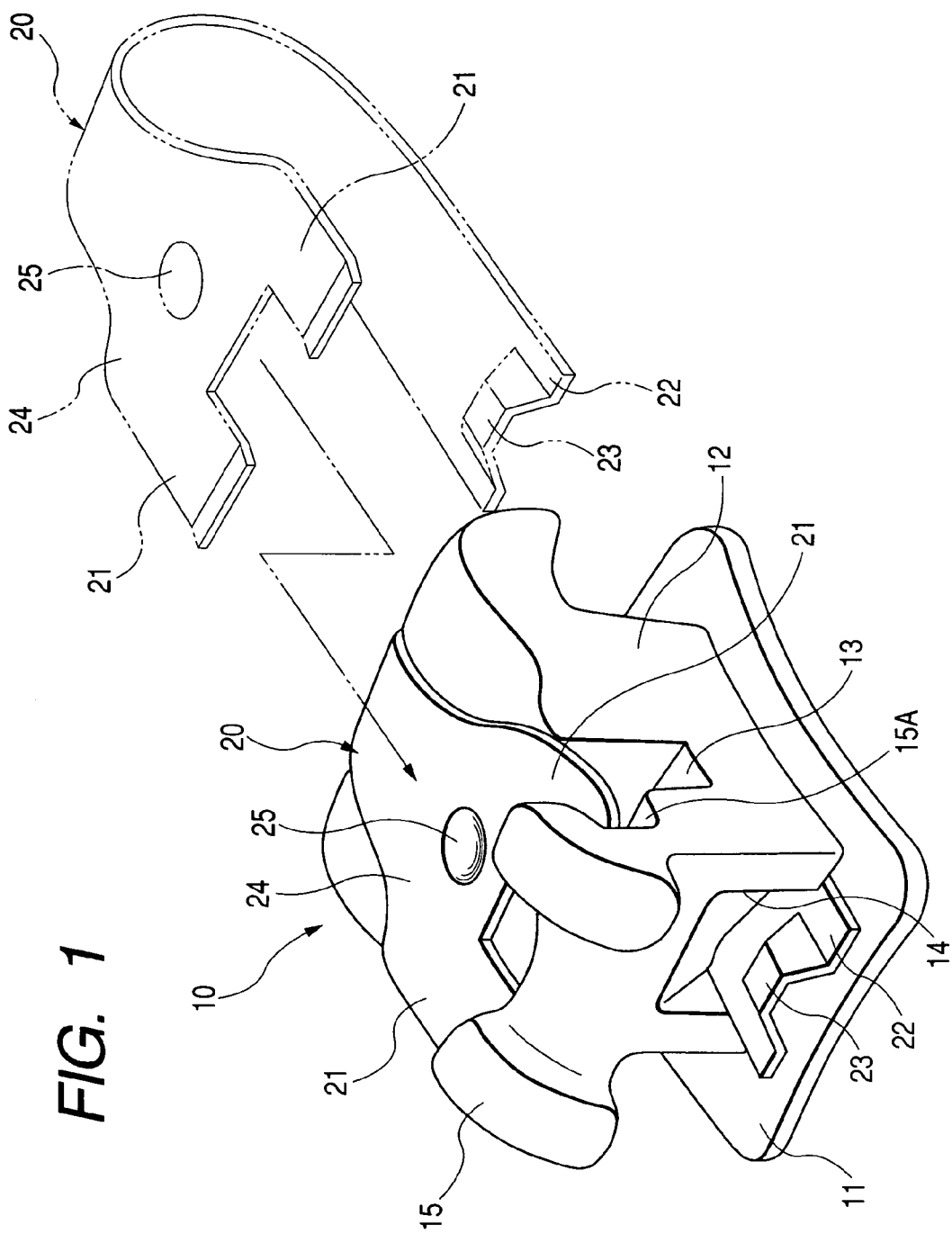
FIG. 1 is a perspective view showing an orthodontic bracket (a first embodiment) according to the invention.

As shown in FIG. 1, an orthodontic bracket 10 as a first embodiment of the invention comprises a base 11, a bracket main body 12, an arch wire slot 13, a guide portion 14, and a substantially belt-like clip 20. The base 11 is firmly attachable directly or indirectly to teeth surfaces. The bracket main body 12 is equipped on one side of the base 11. The arch wire slot 13 is shaped in groove in the bracket main body 12. The guide portion 14 is formed in at least one of the bracket main body and the base, and along a tooth axial direction crossing with the arch wire slot 13. The substantially belt-like clip 20 is guided by the guide portion 14.

The arch wire slot 13 is formed along the mesiodistal direction of the bracket main body 12.

In the orthodontic bracket 10, the clip 20 is curved substantially in U-shape as covering at least one part of an opposite side to the base in the arch wire slot 13. A pair of catching end portions 21 are provided at an upper end part along length of the clip 20. A catching groove 15A is provided at the lower part of a cover portion 15 supported by the bracket main body 12. The pair of catching end portions 21 are caught to enable to creep under the catching groove 15A.

Herein, the opposite side to the base is generally designated as the labial side (the lip side), but in a case of the lingual bracket, it is designated as the lingual side (the tongue side).

The clip 20 is formed to be substantially U-shape with, e.g., a spring thin steel of high corrosion resistance of 0.1 to 0.2 mm thickness.

A base 22 of the clip 20 is inserted into the guide part 14, while the catching end portions 21 creep into the catching groove 15A under the cover part 15. Therefore, the clip 20 is attached to the bracket main body 12 as closing.

The base 22 is provided with an upper projecting stopper 23 so that, when releasing the clip 20, the base 22 does not get out from the guide part 14.

The clip 20 is formed with a concave portion 25 as the recess portion in an upper end part 24 between the pair of catching end portions 21. The concave portion 25 is used for catching a clip release tool 30 (see FIGS. 4 to 7) for releasing the clip 20.

If the recess portion is made concave 25, the clip 20 is not required to have a hole passing through in the thickness direction, so that spring force of the clip 20 can be kept.

Figure 2:
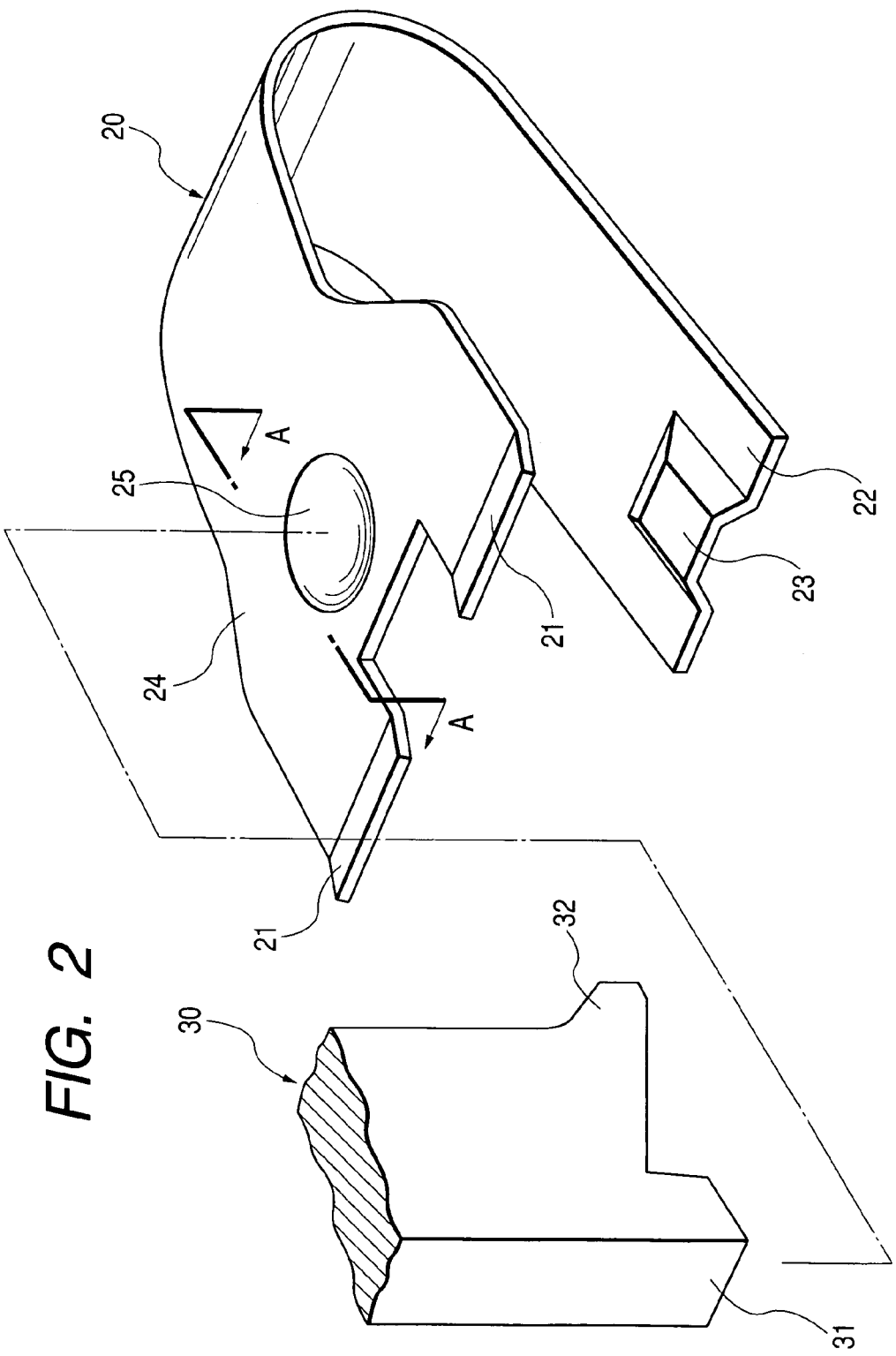
FIG. 2 is a perspective view showing a clip of the first embodiment of the invention.
Figure 3A:
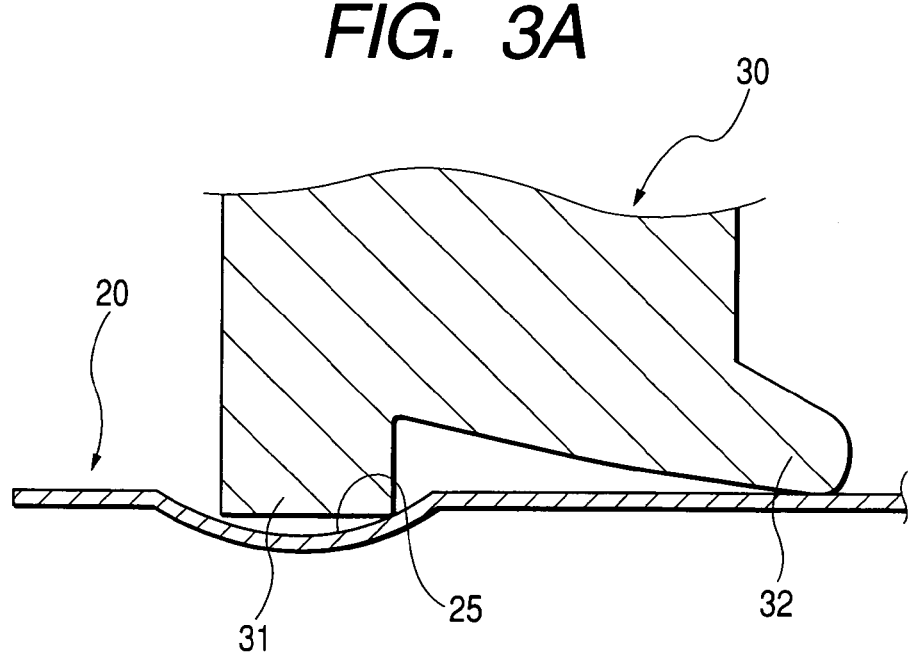
FIG. 3A is a cross sectional view along A-A line of FIG. 2.

As shown in FIGS. 2 and 3A, the concave portion 25 of the clip 20 is formed to be larger than a heel portion 31 of the clip release tool 30 for receiving it.

Thus, if an operator inserts the heel portion 31 of the clip release tool 30 into the concave portion 25 and moves the clip 20 by the clip release tool 30, mutual engagement between the catching end portions 21 of the clip 20 and the catching groove 15A of the cover part 15 (see FIG. 1) can be more certainly and easily canceled.

Herein, a toe portion 32 regulates the engagement of the heel portion 31 to the concave portion 25, and at the same time presses down the clip 20, so that it serves to avoid the clip 20 from deformation.

That is, the toe portion 32 works in a direction of pressing the clip 20 against the bracket main body 12 (see FIG. 1), so that it can be prevented that the clip 20 is turned up by the bar-like tool having referred to concerning the related art, and the clip 20 can be avoided from deformation.

Figure 3B:
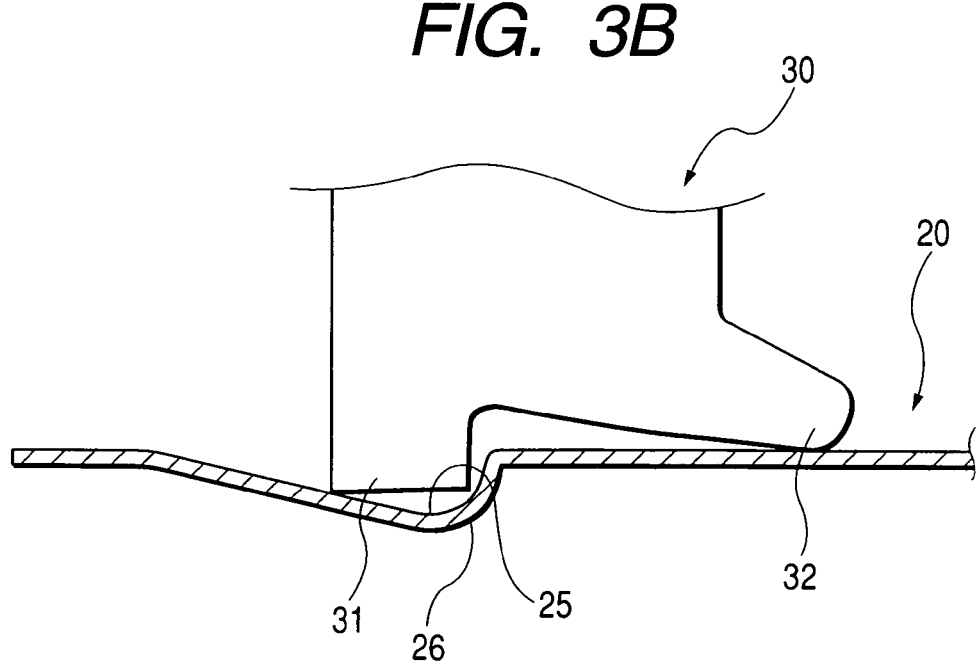
FIG. 3B is a cross sectional view showing a modified example of the first embodiment.

In FIG. 3A, the explanation has been made to the example of forming the concave portion 25 to be circular arc, but no limitation is made to this. For example, as shown in FIG. 3B, it is possible to form a position 26 to be deep toward a side of the toe portion 32 in the concave portion 25.

Thereby, when getting the heel portion 31 into the concave portion 25, the heel portion 31 can be more certainly inserted into the concave portion 31.

Next, the clip release tool 30 will be referred to on the basis of FIGS. 4 to 7B.

As seeing in FIG. 4, the clip release tool 30 has a left releasing portion 34 and a right releasing portion 35 respectively at left and right end parts of a grip 33.

Figure 5A:
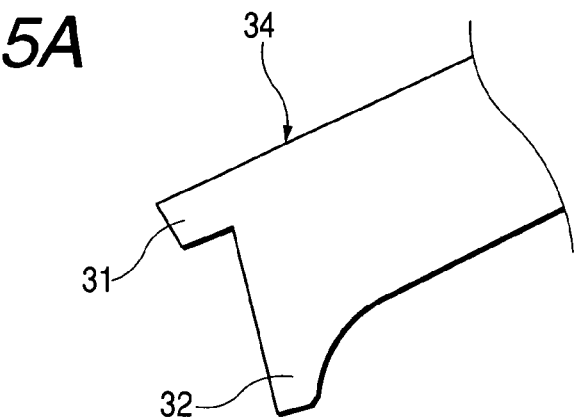
FIGS. 5A and 5B are enlarged views of a portion B of FIG. 4.
Figure 5B:
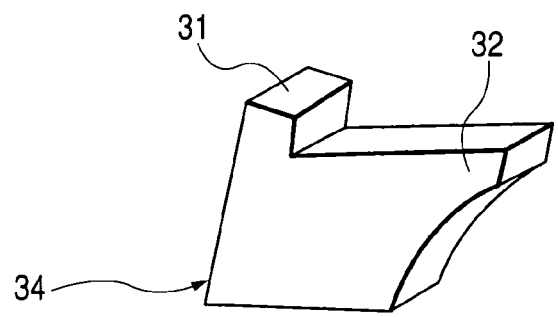

As seeing in FIGS. 5A and 5B, the left releasing portion 34 has a heel portion (a first projection) 31 and a toe portion (a second projection) 32, which are disposed substantially in V-shape and in vertical direction. The heel portion 31 is positioned to enable to catch the concave portion 25 at the upper end part 24 of the clip 20 (see FIGS. 1 and 2).

The toe portion 32 is positioned to regulate the engagement of the heel portion 31 to the concave portion 25 (see FIGS. 1 and 2), and enable to avoid the clip 20 from deformation by pressing down the clip 20 (see FIGS. 1 and 2).

If the heel portion 31 and the toe portion 32 are arranged vertically, the left releasing part 34 can be used in parallel to the tooth axial direction.

The heel portion 31 and the toe portion 32 are formed in the same width.

Figure 6:
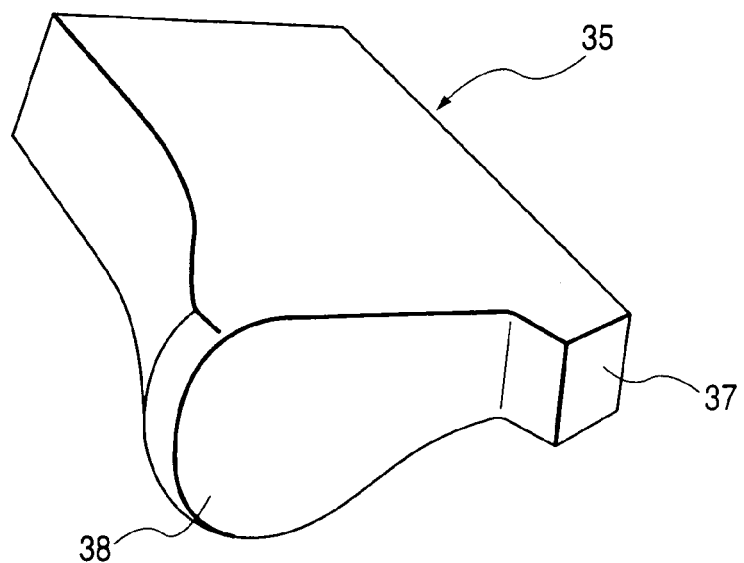
FIG. 6 is an enlarged view of a portion C of FIG. 4.
Figure 7A:
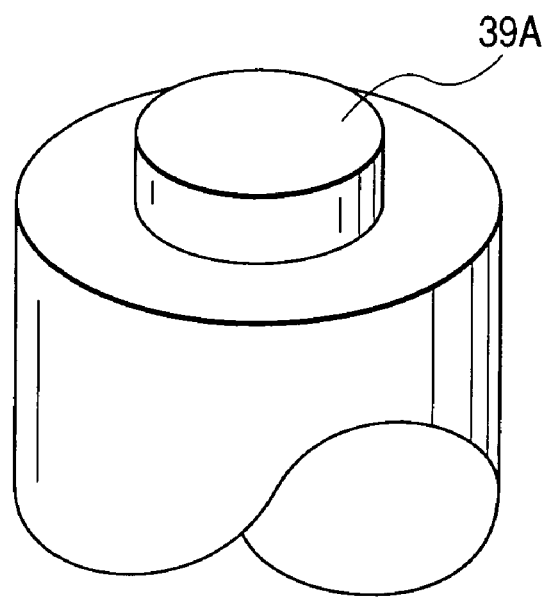
FIGS. 7A and 7B are enlarged views of elementary parts showing modified examples of the clip release tool according to the invention.
Figure 7B:
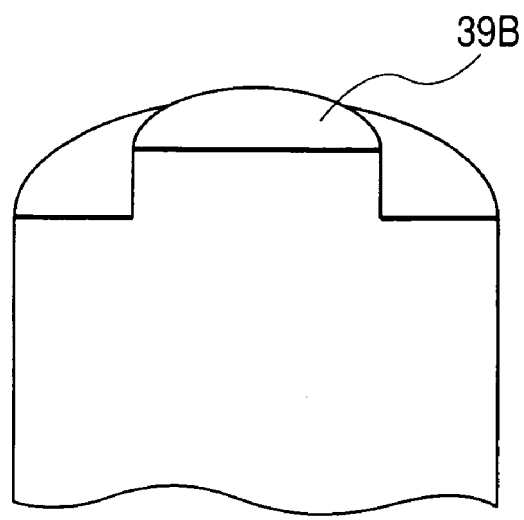

As seeing in FIG. 6, the right releasing part 35 is provided with a heel portion (the first projection) 37 and a toe portion (the second projection) 38, which are disposed substantially in V-shape and in lateral direction. The heel portion 37 is at a position enabling to catch the concave 25 formed in the upper end part 24 of the clip 20 (see FIGS. 1 and 2).

The toe portion 38 is at a position enabling to regulate the engagement of the heel portion 37 with the concave 25 and to avoid deformation of the clip 20 by pressing down the clip 20.

If the heel portion 37 and the toe portion 38 are arranged laterally, it is possible to release the clip 20 in the tooth axial direction from a side in a place not permitting to pull toward a front side such as back tooth.

The heel portion 37 is formed to be narrow in the width and the toe portion 38 is formed to be wide in the width.

In FIGS. 5A, 5B and FIG. 6, the left and right releasing parts 34, 35 have been explained as to the examples formed with the heel portions 31, 37 and the toe portions 32, 38, but no limitation is made thereto. For instance, as seeing in FIG. 7A, a releasing part 39A may be provided with a column limited in height, and as seeing in FIG. 7B, a releasing part 39B may be provided with a half-column limited in height.

In the following, explanation will be made to the heel portion 31 and the toe portion 32 constituting the left releasing part 34 as representative examples.

Next, explanation will be made to works of the orthodontic bracket 10 and the clip release tool 30 on the basis of FIGS. 8A and 8B.

Figure 8A:
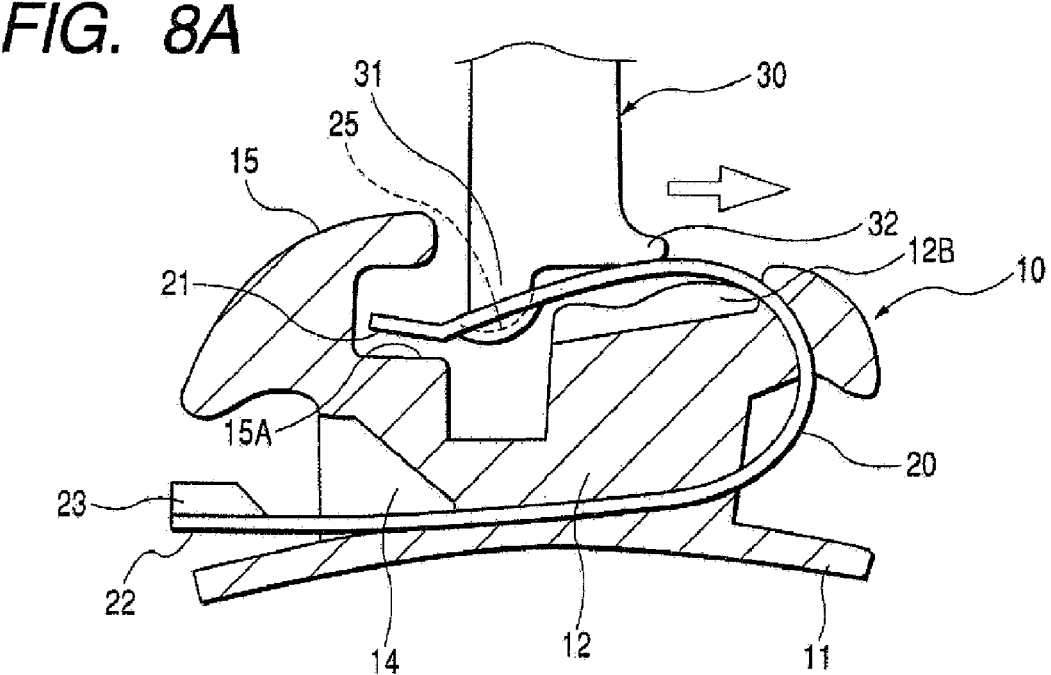
FIGS. 8A and 8B are views for explaining works of the first embodiment of the invention.

In FIG. 8A, the operator gets the heel portion 31 of the clip release tool 30 into the concave portion 25. Then, the toe portion 32 regulates fitting of the heel portion 31 in the concave portion 25.

If moving the clip release tool 30 in a direction of an arrow mark under a condition of getting the heel portion 31 into the concave portion 25, the clip 20 is moved in the arrow direction together with the clip release tool 30.

At this time, the toe portion 32 presses down the clip 20, so that the clip 20 is not turned up, and the clip 20 can be avoided from deformation.

Figure 8B:
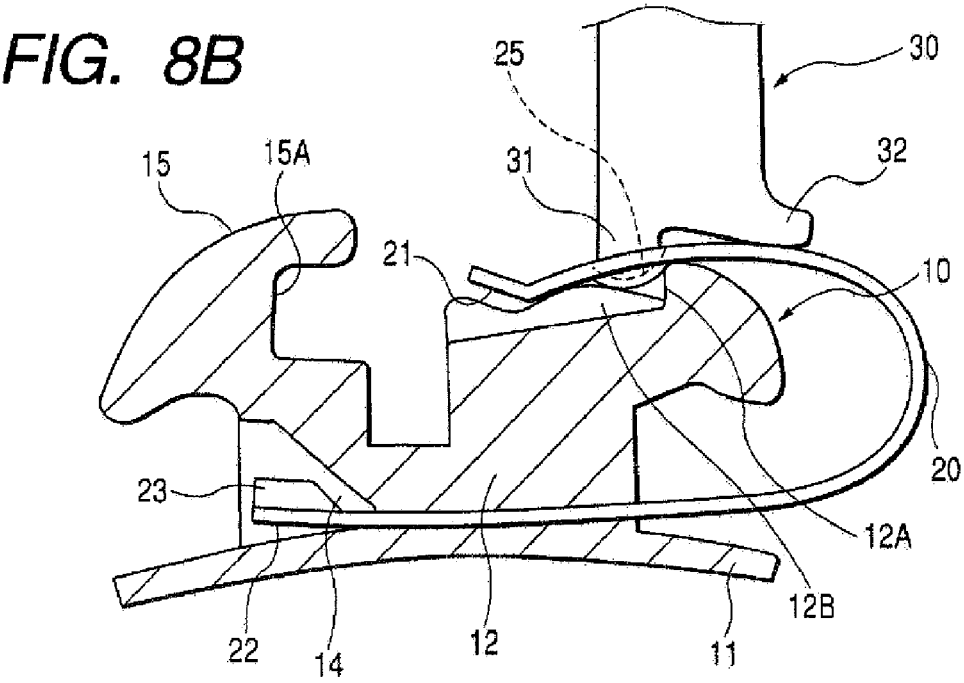

In FIG. 8B, the clip 20 is moved together with the clip release tool 30, and the catching end portions 21 get out from the catching groove 15A of the cover 15 to easily move the clip 20 to the releasing position.

In this case, since the concave portion 25 provided in the clip 20 at the side of the bracket main body 12 is convex, when the clip 20 is released from the bracket main body 12, the releasing position of the clip 20 is regulated in that the concave portion 25 contacts, as the convex, a stepwise receiving portion 12A. It is possible thereby to avoid an exceeding release or drop of the clip 20 from the bracket main body 12. As shown, the stepwise receiving portion 12A is formed at an edge of a middle groove portion 12B that runs in a direction perpendicular to the mesiodistal direction in the bracket main body 12.

Next explanation will be made to second to sixth embodiments of the orthodontic bracket with reference to FIGS. 9 to 15.

Figure 9:
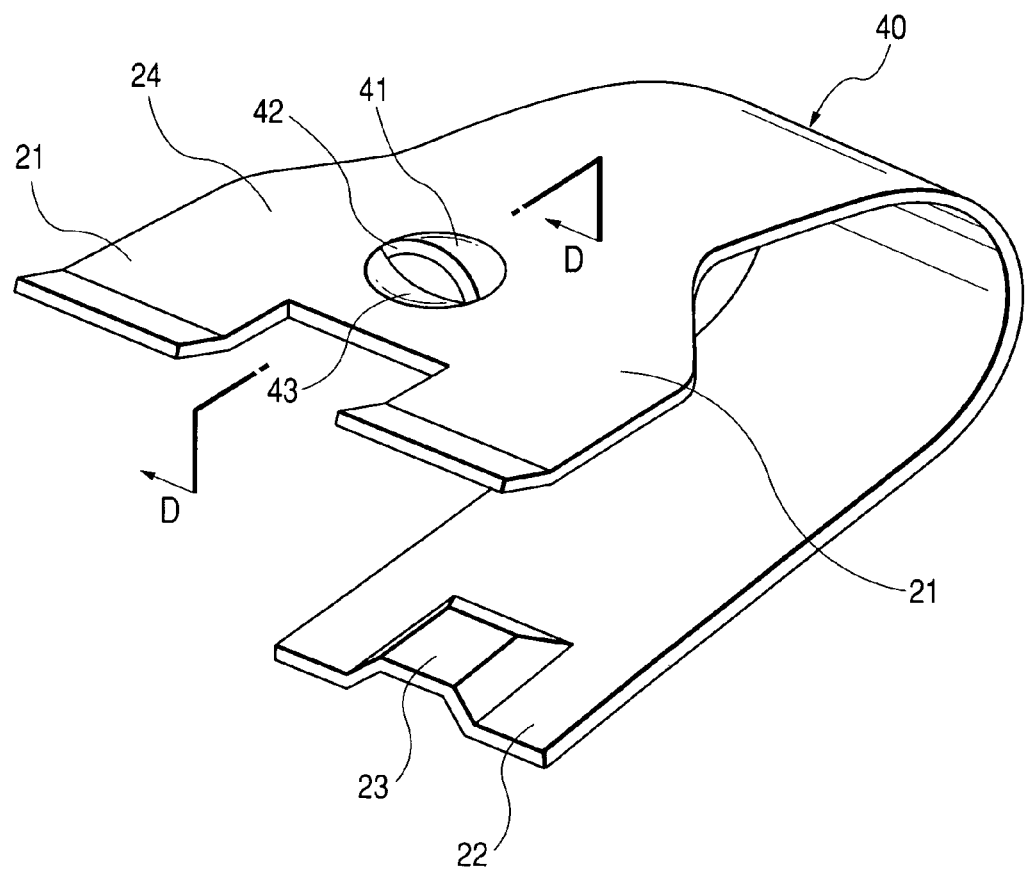
FIG. 9 is a perspective view showing a clip of a second embodiment of the invention.

As shown in FIG. 9, a clip 40 as the second embodiment of the invention is different from the clip 20 of the first embodiment only in that the clip 40 has, as the recess portion, a cut-and-rising portion 41 rising in a direction separating from the bracket main body 12 (see FIG. 1) along the thickness, and other structures are the same as those of the first embodiment.

Figure 10A:
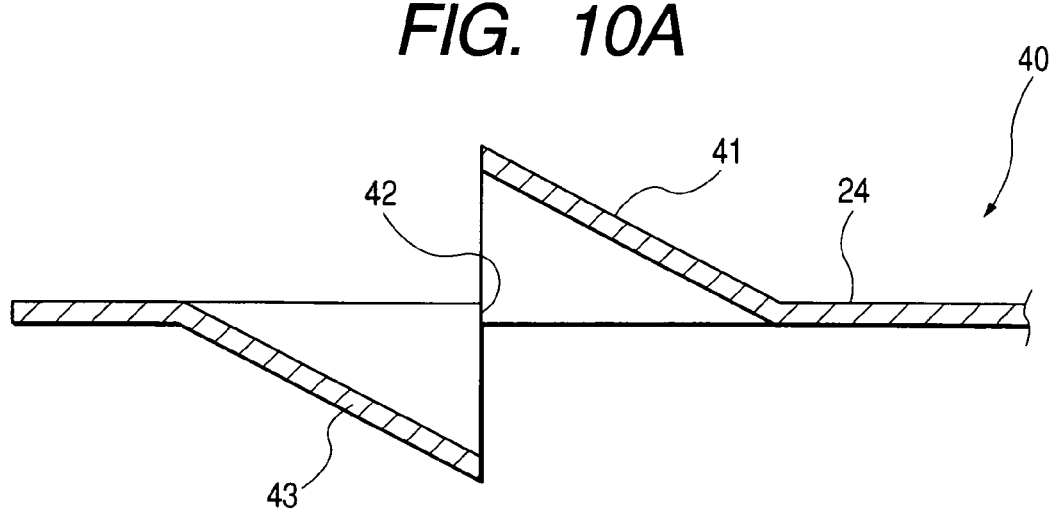
FIG. 10A is a cross sectional view along D-D line of FIG. 9.
Figure 10B:
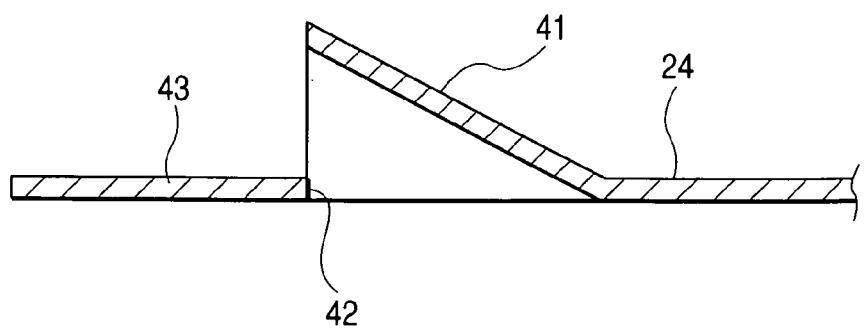
FIG. 10B is across sectional view showing a modified example of the second embodiment.

As shown in FIG. 10A, the cut-and-rising portion 41 is made in the direction separating from the bracket main body 12 (see FIG. 1) along the thickness by raising one side of making a boundary a slit 42 formed in the upper end part 24 of the clip 40.

Herein, the other position 43 having the slit 42 as the boundary is raised in the direction approaching the bracket main body 12 along the thickness.

In FIGS. 9 and 10A, the explanation has been made to the example that the other position 43 having the slit 42 as the boundary is raised in the direction approaching the bracket main body 12 along the thickness, and no limitation is made thereto. For example, as seeing in FIG. 10B, the same effect is available although the other position 43 having the slit 42 as the boundary is not raised in the direction approaching the bracket main body 12 along the thickness.

Figure 11A:
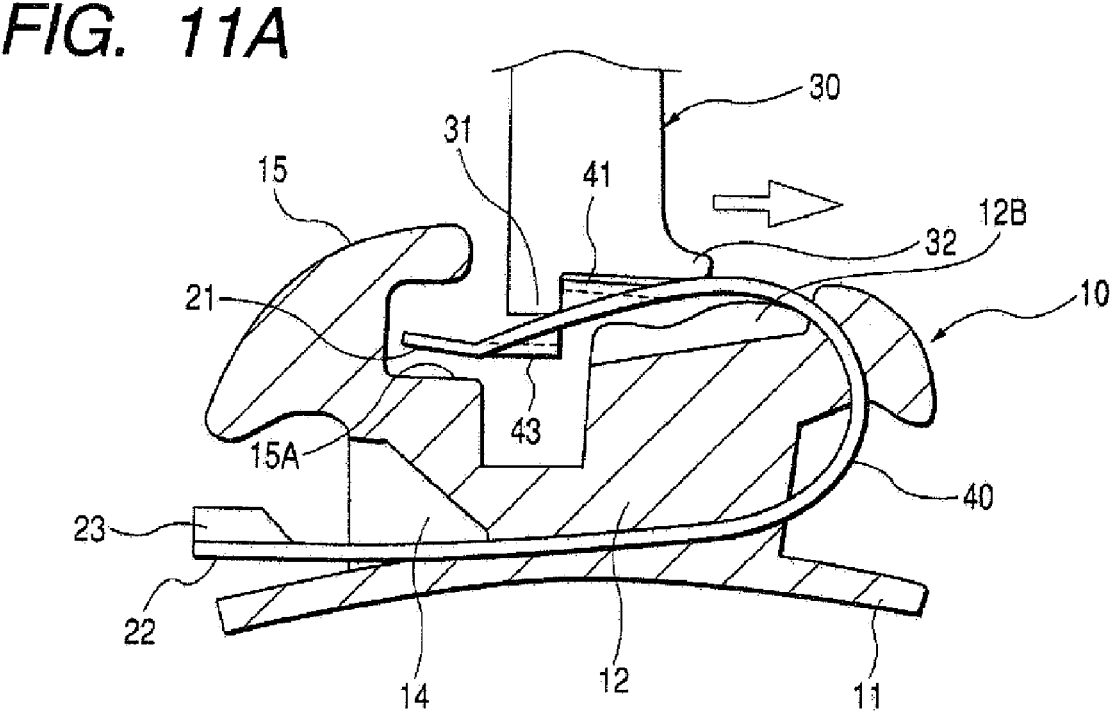
FIGS. 11A and 11B are views for explaining works of the second embodiment of the invention.
Figure 11B:
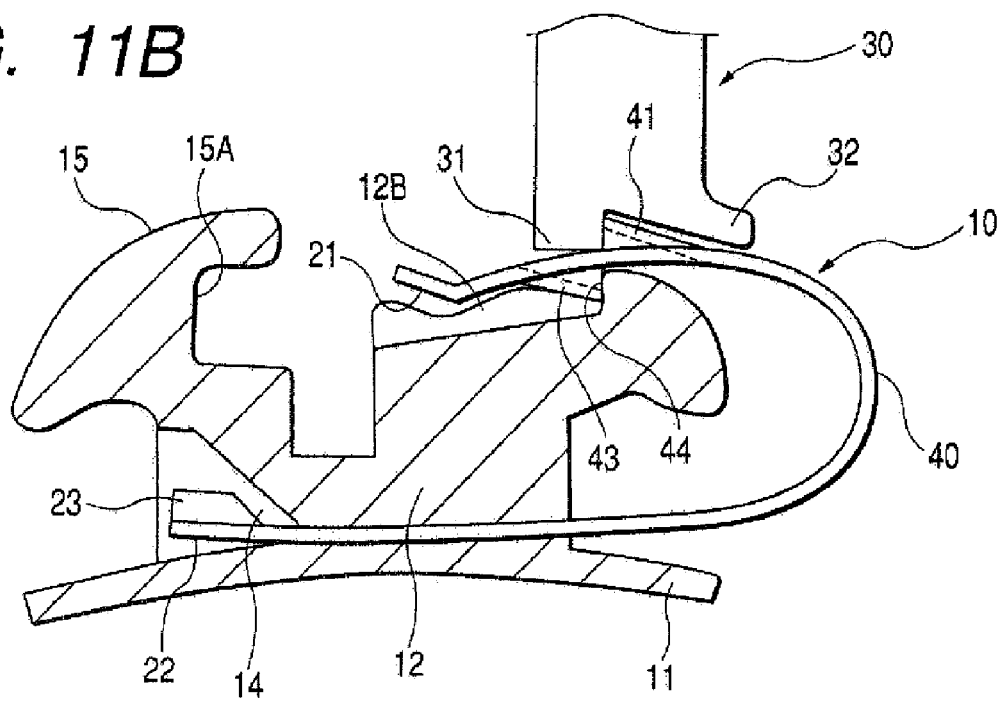

Further explanation will be referred to works of the clip 40 on the basis of FIGS. 11A and 11B.

In FIG. 11A, the operator disposes the heel portion 31 of the clip release tool 30 neighboring the cut-and-rising portion 41, so that the heel portion 31 contacts the cut-and-rising portion 41.

In this case, the toe portion 32 regulates engagement of the heel portion 31 with the other position 43.

Under this condition, if moving the clip release tool 30 in the arrow direction, the clip 40 is moved in the same together with the clip release tool 30.

Then, the toe portion 32 can press down the clip 40 to prevent it from turning up and enable to avoid deformation of the clip 40.

In FIG. 11B, the catching end portions 21 of the clip 40 slips out of the catching groove 15A of the cover part 15, and can easily move the clip 40 to the releasing position.

At this time, the other position 43 can be used as a stopper.

That is, the other position 43 contacts a wall 44 of a middle groove terminal to stop the clip 40. Thus, a sliding range is reasonably limited, enabling to prevent the clip 40 from exceedingly releasing.

It is possible thereby to avoid the clip from deformation caused by the clip over releasing.

In addition, also in the clip 40 of the second embodiment, the same effect as that of the clip 20 of the first embodiment can be obtained.

Next, a third embodiment will be referred to.

Figure 12:
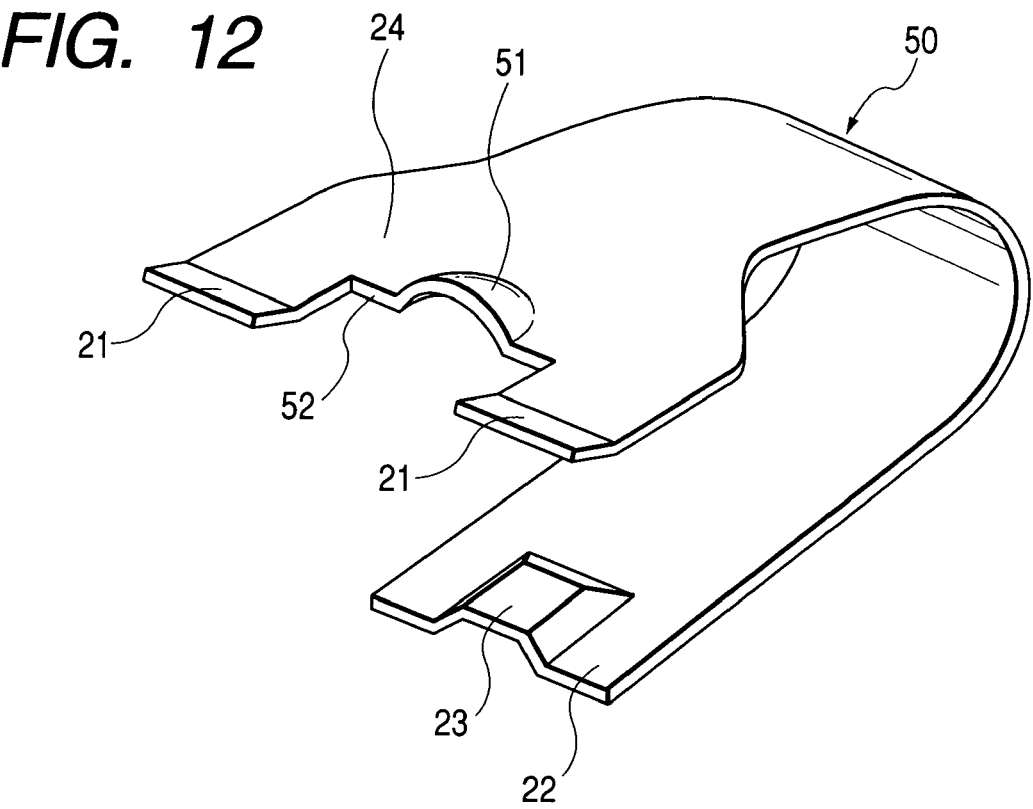
FIG. 12 is a perspective view showing a clip of a third embodiment of the invention.

As shown in FIG. 12, a clip 50 as the third embodiment of the invention is different from the clip 20 of the first embodiment only in that the clip 50 has, as the recess portion, a cut-and-rising portion 51 rising in a direction separating from the bracket main body 12 (see FIG. 1) along the thickness, and other structures are the same as those of the first embodiment.

The cut-and-rising portion 51 is provided substantially in a half-spherical dome shape at an end part 52 of the clip 50.

If the clip release tool 30 is moved under a condition of contacting the heel portion 31 (see FIG. 2) to the cut-and-rising portion 51, the clip 50 can be released together with the clip release tool 30.

In the clip 50 of the third embodiment, the same effect as that of the clip 20 of the first embodiment can be also obtained.

Next, a fourth embodiment will be referred to.

Figure 13:
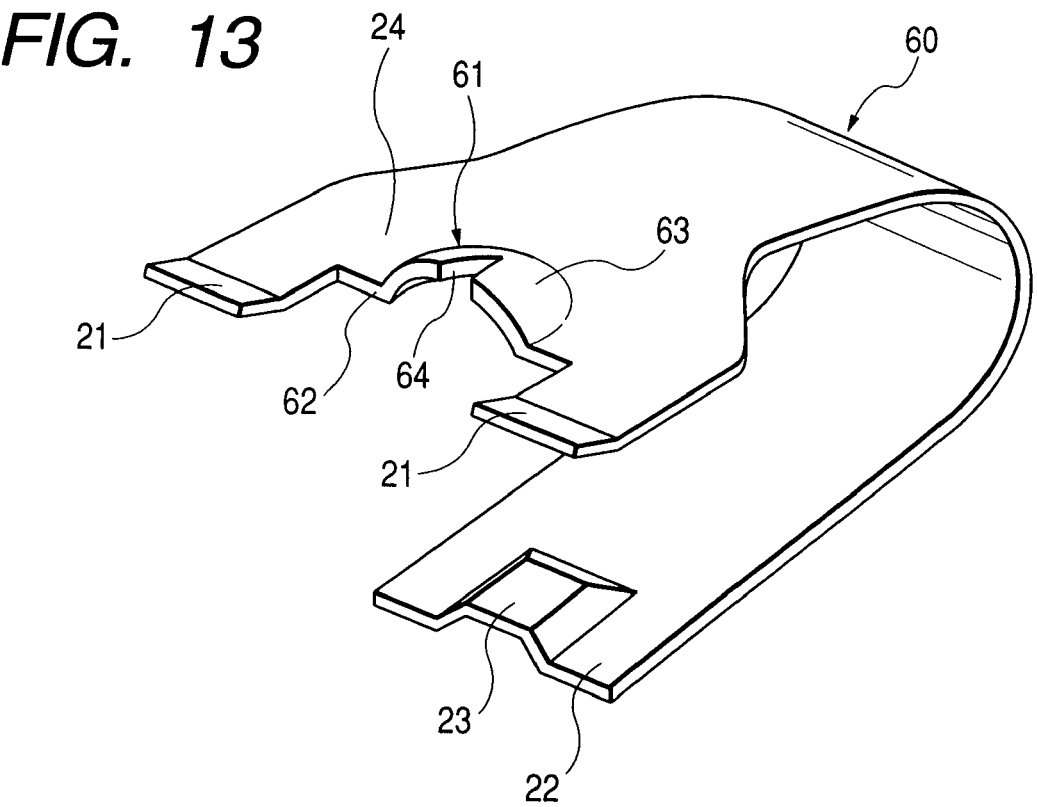
FIG. 13 is a perspective view showing a clip of a fourth embodiment of the invention.

As shown in FIG. 13, a clip 60 as the fourth embodiment of the invention is different from the clip 20 of the first embodiment only in that the clip 60 has, as the recess portion, a cut-and-rising portion 61 rising in a direction separating from the bracket main body 12 (see FIG. 1) along the thickness, and other structures are the same as those of the first embodiment.

The cut-and-rising portion 61 is provided substantially in a half-spherical dome shape at an end part 62 of the clip 60, and a cutout portion 64 substantially in V-shape is provided in a flat end part 63 of the cut-and-rising portion 61.

If the clip release tool 30 is moved under a condition of contacting the heel portion 31 (see FIG. 2) to the cut-and-rising portion 61, the clip 60 can be released together with the clip release tool 30.

In this case, since the substantially V-shaped cutout 64 is provided in the flat end part 63 of the cut-and-rising portion 61, the heel portion 31 is held by the cutout portion 64 and can be certainly caught with the cut-and-rising portion 61, so that handling can be more heightened.

In the clip 60 of the fourth embodiment, the same effect as that of the clip 20 of the first embodiment can be also obtained.

A fifth embodiment will be explained.

Figure 14:
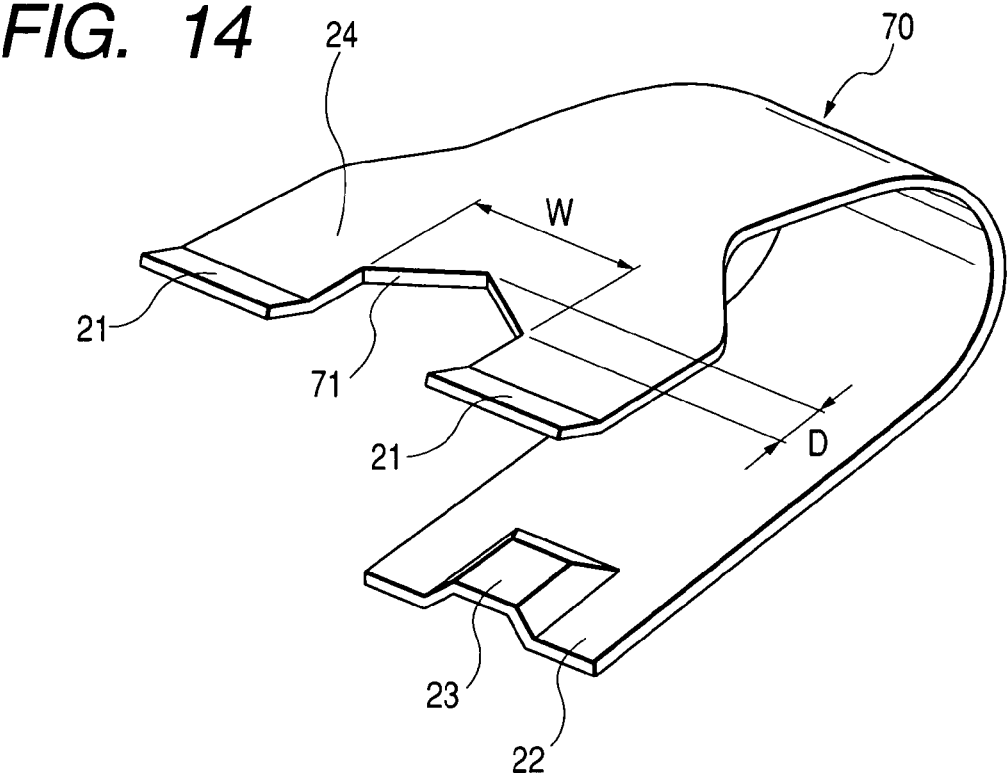
FIG. 14 is a perspective view showing a clip of a fifth embodiment of the invention.

As shown in FIG. 14, a clip 70 as the fifth embodiment of the invention is different from the clip 20 of the first embodiment only in that the upper end part 24 is provided with a catching cutout portion 71 substantially in V-shape enabling to catch the heel portion 31 (see FIG. 2) of the clip release tool 30 for releasing the clip 70, and other structures are the same as those of the first embodiment.

The catching cutout portion 71 is determined to be 0.5 to 2.0 mm in width W and 0.3 to 1.0 mm in depth D.

By determining the width W of the catching cutout portion 71 to be 0.5 to 2.0 mm and the depth D 0.3 to 1.0 mm, spring force of the clip 20 can be effectively transmitted to the catching end portions 21 formed at the upper end parts of the clip 20 divided in the mesiodistal direction.

If the clip release tool 30 is moved under a condition of contacting the heel portion 31 (see FIG. 2) to the catching cutout portion 71, the clip 70 can be released together with the clip release tool 30.

Thus, since the catching cutout portion 71 is formed substantially in V-shape, the heel portion 31 is held by the catching cutout portion 71, so that the handling can be more heightened.

In the clip 70 of the fifth embodiment, the same effect as that of the clip 20 of the first embodiment can be also obtained.

Next, a sixth embodiment will be referred to.

Figure 15:
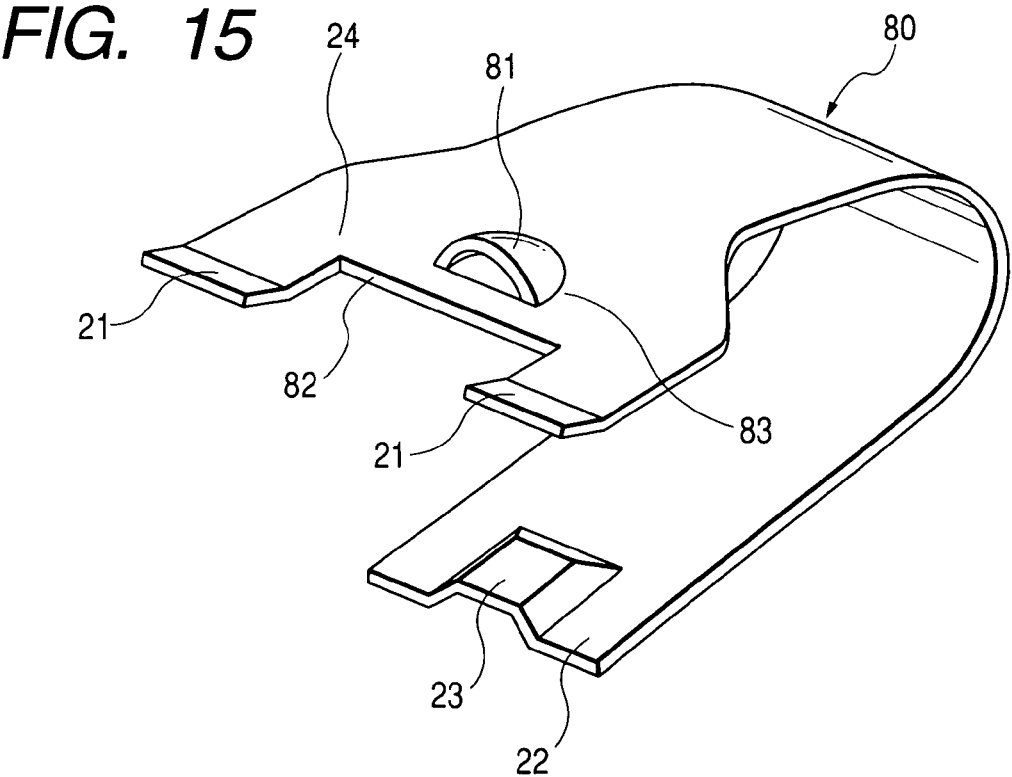
FIG. 15 is a perspective view showing a clip of a sixth embodiment of the invention.

As shown in FIG. 15, a clip 80 as the sixth embodiment of the invention is different from the clip 20 of the first embodiment only in that the clip 80 is a cut-and-rising portion 81 rising in a direction separating from the bracket main body 12 (see FIG. 1) along the thickness, and other structures are the same as those of the first embodiment.

The cut-and-rising portion 81 is provided substantially in a half-spherical dome shape at a part 83 separating from the end part 82 of the clip 80.

If the clip release tool 30 is moved under a condition of contacting the heel portion 31 (see FIG. 2) to the cut-and-rising portion 81, the clip 80 can be released together with the clip release tool 30.

In the clip 80 of the sixth embodiment, the same effect as that of the clip 20 of the first embodiment can be also obtained.

The clip release tool and other embodiments will be explained on the basis of FIGS. 16 to 18.

Figure 16:
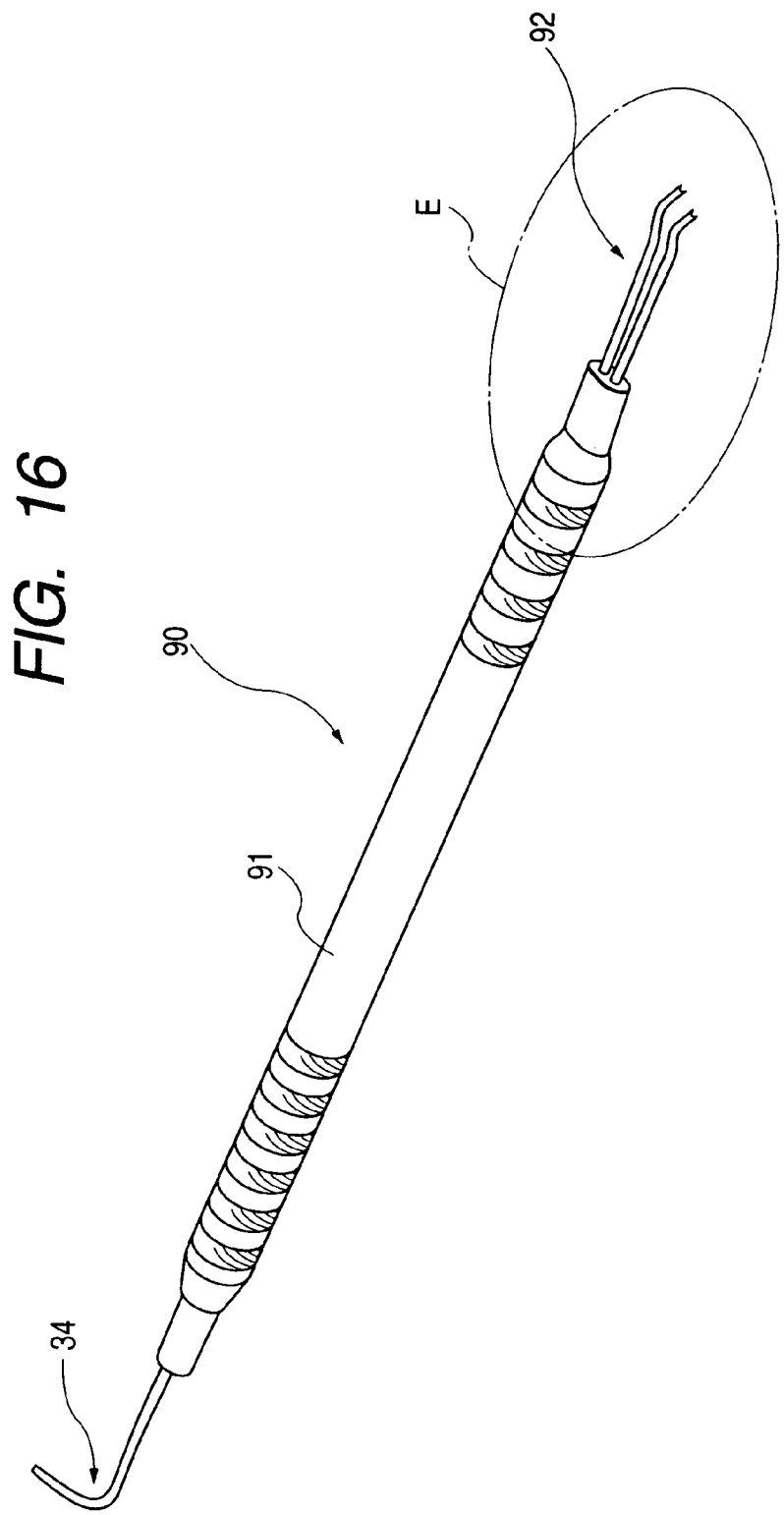
FIG. 16 is a perspective view showing a modified example of the clip release tool according to the invention.

As seeing in FIG. 16, a clip release tool 90 has, for example, a left releasing portion 34 (see FIG. 4) at the left end part of a grip 91, and a wire releasing portion 92 at the right end part.

Figure 17:
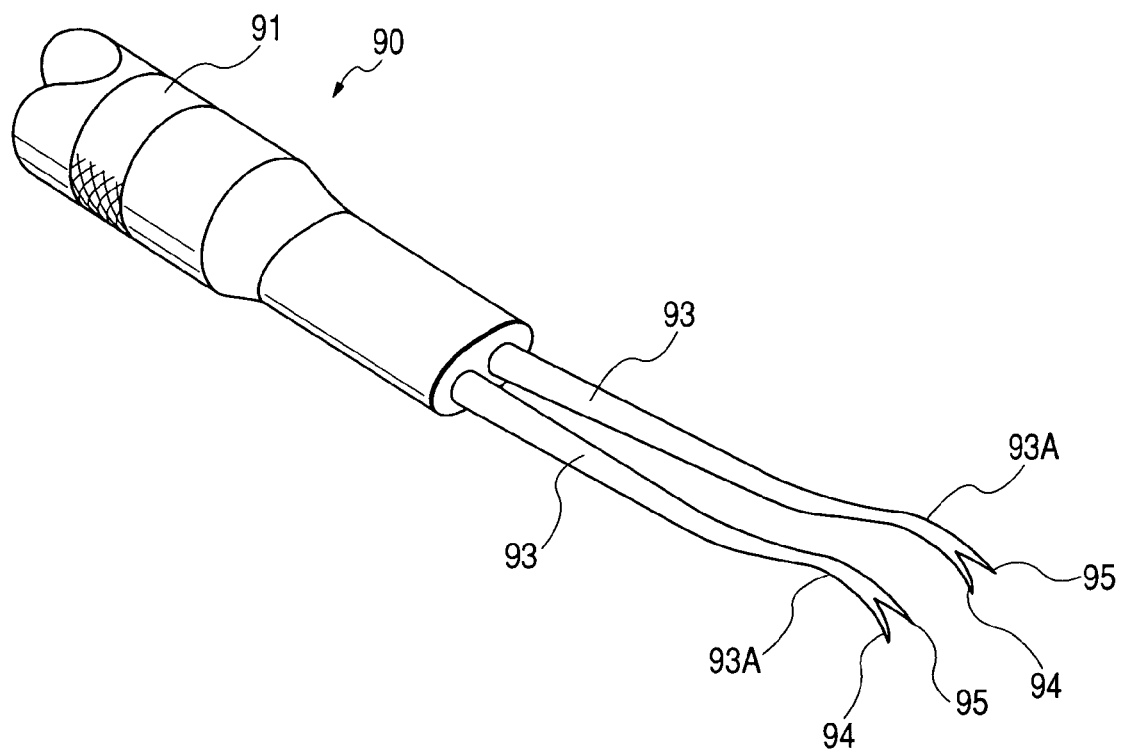
FIG. 17 is an enlarged view of a portion E of FIG. 16.

As seeing in FIG. 17, the wire releasing portion 92 has respectively first projections 94 and second projections 95 substantially in V-shape at distal parts 93A of a pair of rods 93.

The pair of rods 93 are, as shown in FIG. 18, positioned at the front end portions 93A thereof to both sides of the orthodontic bracket 10 disposed on the tooth 97. An arch wire 98 is placed between the first and second projections 94, 95 of one rod 93, while the arch wire 98 is similarly placed between the first and second projections 94, 95 of the other rod 93.

By using the clip release tool 90 thereby, the arch wire 98 can be easily adjusted.

A seventh embodiment of the orthodontic bracket will be explained on the basis of FIGS. 19A to 19C.

Figure 19A:
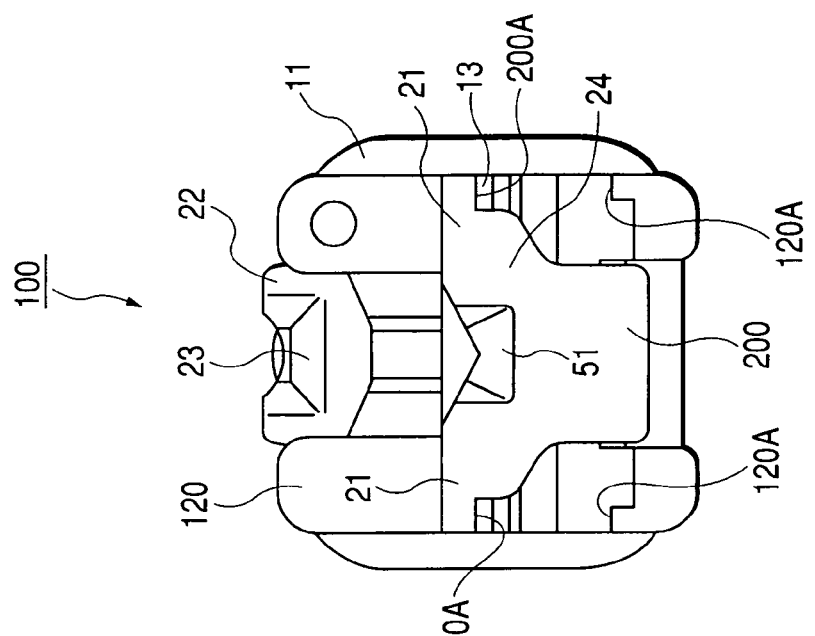
FIGS. 19A to 19C are plan and side views showing an orthodontic bracket (a seventh embodiment) according to the invention.
Figure 19B:
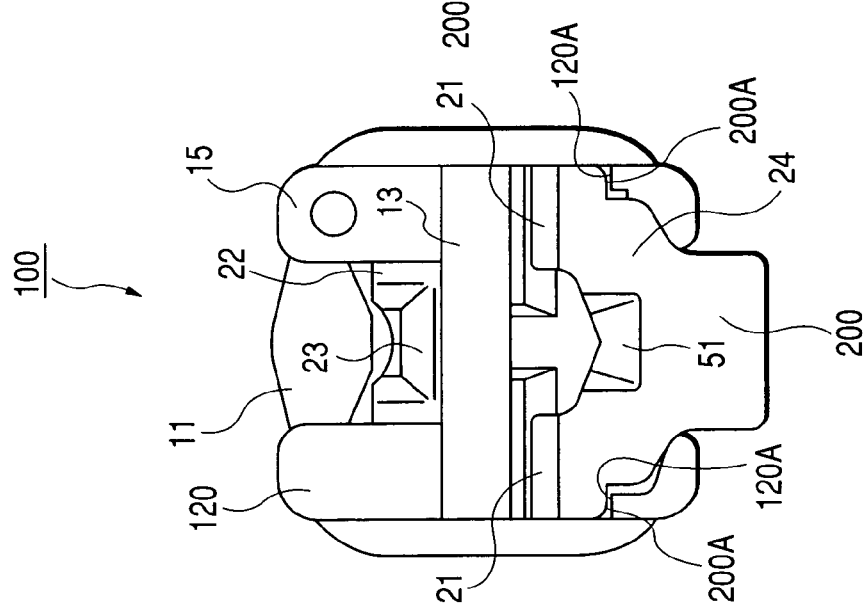
Figure 19C:
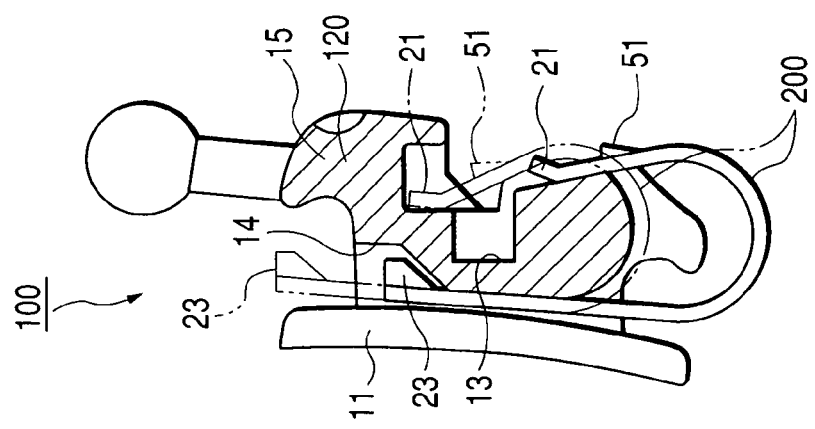

The orthodontic bracket 100 shown in FIGS. 19A to 19C has a bracket main body 120 basically similar to the bracket main body 12 used in the orthodontic bracket 10 of the first embodiment and a clip 200 similar to the clip 50 exemplified in the third embodiment.

The orthodontic bracket 100 is different from those of the first and third embodiments in that a pair of contacting portions 200A is furnished in the clip 200 and the bracket main body 120 has a pair of receiving portions 120A enabling to contact with the respective contacting portions 200A.

The contacting portions 200A are provided as cutouts substantially like a crank in flat at an end part of the clip 200 formed as expanding toward the upper end of the clip 200. On the other hand, the receiving portions 120A are stepwise portions formed in the surface of the bracket main body 120, and the flat shape thereof corresponds to the flat shape of the contacting portions 200A (see FIG. 19C).

Therefore, the contacting portion 200A and the receiving portion 120A contact each other when the clip 200 is released until a predetermined position from the bracket main body 120, thereby to regulate the releasing position of the clip 200 from the bracket main body 120 (see FIGS. 19A and 19B).

When releasing the clip 200 from the bracket main body 120, the respective contacting portions 200A contact the respective receiving portion 120A. Therefore, the orthodontic bracket 100 regulates the releasing position of the clip 200 from the bracket main body 120, and it is possible to avoid the over-releasing or dropping of the clip 200 from the bracket main body 120.

As to other matters, qualities of materials, dimensions, configurations, numbers, arranging places, thickness sizes, and others of the clips, clip release tools, or bracket main bodies exemplified in the above embodiments may be arbitrary without making any limitations as far as accomplishing the invention.

As explained above, according to the orthodontic bracket of the first aspect of the invention, the clip is provided at the upper end part thereof with the recess portion which enables to catch the clip release tool for releasing the clip. The position catching the clip release tool is formed to be the recess, so that it is not required to open a hole for the clip to pass through in the thickness direction. Thus, it keeps rigidity and can secure spring force.

Besides, since the clip is not opened with the hole but formed with the recess portion, concentration of stress is not loaded to the recess portion of the clip, so that the clip can be prevented from deformation.

The spring force of the clip is secured, and the stress is not concentrated, thereby enabling to avoid the clip from deformation.

According to the orthodontic bracket of the second aspect of the invention, the recess portion is made the concave, so that the recess portion can be comparatively easily formed and the clip can be comparatively easily formed, it is possible to reduce the cost-up, prevent the clip from deformation, and secure the spring force of the clip.

According to the orthodontic bracket of the third aspect of the invention, the recess portion is made the cut-and-rising portion in the direction separating from the bracket main body, so that the recess portion can be comparatively easily formed. The clip can be comparatively easily formed, and it is possible to reduce the cost-up, prevent the clip from deformation, and secure the spring force of the clip.

According to the orthodontic bracket of the fourth aspect of the invention, the recess portion is the cut-and-rising portion which causes one side of the slit as the boundary formed at the upper end part of the clip to rise along thickness in a direction separating from the bracket main body, so that the clip can be comparatively easily formed. It is possible to reduce the cost-up, prevent the clip from deformation, and secure the spring force of the clip.

According to the orthodontic bracket of the fifth aspect of the invention, the recess portion is formed at the end part of the clip, so that the recess portion can be more easily formed. Therefore, the cost-up can be reduced, and the exclusively used tool can be positioned accurately there at its front end.

According to the orthodontic bracket of the sixth aspect of the invention, the recess portion is shaped substantially in the half-spherical dome. Therefore, the clip release tool can be easily caught by the recess portion, making use of the substantially half-spherical dome. Thereby, when releasing the clip, it is possible to more easily release the clip.

According to the orthodontic bracket of the seventh aspect of the invention, the recess portion is formed with the cutout, so that the clip release tool can be easily caught by the recess portion. Thereby, when releasing the clip, it is possible to more easily release the clip.

According to the orthodontic bracket of the eighth aspect of the invention, the clip is formed at the upper end part thereof with the catching cutout portion substantially in V-shape which enables to catch the clip release tool for releasing the clip. Therefore, the recess portion can be more easily formed, so that the clip can be easily formed, thereby enabling to reduce the cost-up.

According to the orthodontic bracket of the ninth aspect, when the clip is released from the bracket main body, the contacting portion contacts the receiving portion, thereby enabling to regulate the releasing position of the clip from the bracket main body. Therefore, it is possible to prevent the clip from exceedingly releasing from the bracket main body, and the clip from dropping from the bracket main body.

According to the clip release tool of the ten aspect of the invention, it comprises the first projection and the second projection arranged substantially in V-shape. The first projection is caught with the recess portion or the catching cutout potion, and the second projection regulates the engagement of the first projection with the recess portion or the catching cutout portion.

Pressing the clip with the second projection, when releasing the clip, the clip is prevented from tuning up and deformation.

What is claimed is:

1. An orthodontic bracket comprising:
   a base firmly attachable directly or indirectly to teeth surfaces;
   a bracket main body equipped on one side of the base;
   an arch wire slot shaped as a groove along a mesiodistal direction in the bracket main body, operative to support an arch wire therein;
   a substantially belt-like clip curved substantially in a U-shape to cover at least one part of the arch wire slot that opposes the base, the clip having a catching end portion, at an upper end part of the clip, operative to creep under a cover portion of the bracket main body, and a recess portion, at the upper end part of the clip, operative to catch a clip release tool for releasing the clip;
   a guide portion formed in at least one of the bracket main body and the base, the guide portion provided along a tooth axial direction crossing with the arch wire slot, the guide portion operative to guide the clip;
   a middle groove, formed on the bracket main body at a middle area thereof along a direction perpendicular to the mesiodistal direction; and
   a wall portion which extends upward from an edge of the middle groove and faces the cover portion,
   wherein the bracket main body has a front end portion and a rear end portion, the front end portion being separated from the rear end portion by the arch wire slot, and
   wherein the cover portion is provided at the front end portion and the edge from which the wall portion extends is provided at the rear end portion, and wherein the wall portion extends in a direction perpendicular to the mesiodistal direction and perpendicular the direction of the middle groove.

2. The orthodontic bracket as set forth in claim 1, wherein the recess portion is a concave portion which does not pass through the clip in a thickness direction.

3. The orthodontic bracket as set forth in claim 1, wherein the recess portion is a cut-and-rising portion comprising a convex portion that protrudes from an outer surface of the clip in a direction facing away from the bracket main body.

4. The orthodontic bracket as set forth in claim 3, wherein the convex portion is formed at an edge of the upper end part of the clip.

5. The orthodontic bracket as set forth in claim 3, wherein the convex portion is formed at an end part of the clip.

6. The orthodontic bracket as set forth in claim 5, wherein the convex portion is shaped substantially in a half-spherical dome.

7. The orthodontic bracket as set forth in claim 5, wherein the convex portion has a cutout substantially in a V-shape at a flat end part thereof.

8. An orthodontic bracket comprising:
   a base firmly attachable directly or indirectly to teeth surfaces;
   a bracket main body equipped on one side of the base;
   an arch wire slot shaped as a groove along a mesiodistal direction in the bracket main body, operative to support an arch wire therein;
   a substantially belt-like clip curved substantially in a U-shape to cover at least one part of the arch wire slot that opposes the base, the clip having a catching end portion, at an upper end part of the clip, operative to creep under a cover portion of the bracket main body, and a catching cutout portion, in the upper end part of the clip, substantially in a V-shape for catching a clip release tool for releasing the clip;
   a guide portion formed in at least one of the bracket main body and the base, the guide portion provided along a tooth axial direction crossing with the arch wire slot, the guide portion operative to guide the clip;
   a middle groove, formed on the bracket main body at a middle area thereof along a direction perpendicular to the mesiodistal direction; and
   a wall portion which extends upward from an edge of the middle groove and faces the cover portions
   wherein the bracket main body has a front end portion and a rear end portion, the front end portion being separated from the rear end portion by the arch wire slot, and
   wherein the cover portion is provided at the front end portion and the edge from which the wall portion extends is provided at the rear end portion, and wherein the wall portion extends in a direction perpendicular to the mesiodistal direction and perpendicular the direction of the middle groove.

9. The orthodontic bracket as set forth in claim 1, wherein the clip has a contacting portion, and wherein when the clip is released from the bracket main body, the contacting portion contacts to the wall portion, thereby regulating a releasing position of the clip from the bracket main body.

10. The orthodontic bracket as set forth in claim 8, wherein the clip has a contacting portion, and wherein when the clip is released from the bracket main body, the contacting portion contacts to the wall portion, thereby regulating a releasing position of the clip from the bracket main body.

11. The orthodontic bracket as set forth in claim 3, where the cut-and-rising portion also comprises a concave portion connected to the convex portion.

12. The orthodontic bracket as set forth in claim 1, wherein the cover portion does not cover the recess portion.

13. The orthodontic bracket as set forth in claim 8, wherein the catching cutout portion extends from an edge of the upper end part of the clip.

14. The orthodontic bracket as set forth in claim 1, where the clip does not come into contact with the bracket main body before moving the clip to a releasing position.

15. The orthodontic bracket as set forth in claim 8, where the clip does not come into contact with the bracket main body before moving the clip to a releasing position.

* * * * *